(12) United States Patent
Warren

(10) Patent No.: US 8,722,630 B2
(45) Date of Patent: May 13, 2014

(54) USE OF APOLIPOPROTEINS TO DECREASE INFLAMMATION

(75) Inventor: H. Shaw Warren, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 36 days.

(21) Appl. No.: 12/997,821

(22) PCT Filed: Jun. 15, 2009

(86) PCT No.: PCT/US2009/047341
§ 371 (c)(1),
(2), (4) Date: Mar. 30, 2011

(87) PCT Pub. No.: WO2009/152493
PCT Pub. Date: Dec. 17, 2009

(65) Prior Publication Data
US 2011/0195893 A1    Aug. 11, 2011

Related U.S. Application Data

(60) Provisional application No. 61/131,901, filed on Jun. 13, 2008.

(51) Int. Cl.
*A61K 38/16* (2006.01)
*A61K 38/00* (2006.01)

(52) U.S. Cl.
USPC ........................................ 514/21.2; 514/16.4

(58) Field of Classification Search
None
See application file for complete search history.

(56) References Cited

U.S. PATENT DOCUMENTS

| | | |
|---|---|---|
| 6,423,830 B1 | 7/2002 | Winge et al. |
| 2003/0109442 A1 | 6/2003 | Bisgaier et al. |
| 2003/0165503 A1 | 9/2003 | Fruchart et al. |
| 2004/0204355 A1 | 10/2004 | Tracey et al. |
| 2005/0228473 A1 * | 10/2005 | Brown ........................ 623/1.2 |

FOREIGN PATENT DOCUMENTS

WO  WO 2007/111938 A2   10/2007

OTHER PUBLICATIONS

Ansell et al. 2007. Current Atherosclerosis Reports 9:57-63.*
Ansell. 2007. Am J. Cardiol. 100[suppl]:3N-9N.*
Ooi et al. 2008. Clin Sci 114:611-624.*
Mello et al. 2011 Atherosclerosis 215:257-263.*
Kawakami et al 2009 J. Ather. And Thromb. 16:6-11.*
Nissen et al. 2003. JAMA 290:2292-2300.*
Mulvihill et al. 2002. Heart 87:201-204.*
Slysh et al 1985. Am. Heart J. 109:744-52.*
Navab et al. 2002. Circulation 105:290-292.*
Navab et al. 2005. Arterioscler Thromb Vasc Biol. 25:1932-1937.*
Barter et al., "Antiinflammatory properties of HDL," *Circulation Research* 95:764-772 (2004).
Berbée et al., "Apolipoproteins modulate the inflammatory response to lipopolysaccharide," *Journal of Endotoxin Research* 11(2):97-103 (2005).
Birjmohun et al., "Apolipoprotein A-II is inversely associated with risk of future coronary artery disease," *Circulation* 116:2029-2035 (2007).
Boisfer et al., "Antioxidant properties of HDL in transgenic mice overexpressing human apolipoprotein A-II," *J. Lipid Res.* 43:732-741 (2002).
Calabresi et al., "Inhibition of VCAM-1 expression in endothelial cells by reconstituted high density lipoproteins," *Biochem. Biophys. Res. Commun.* 238:61-65 (1997).
Furlaneto et al., "Apolipoproteins A-I and A-II downregulate neutrophil functions," *Lipids* 37(9):925-928 (2002).
Guo-Fen et al., "Effect of acute inflammation on rat apolipoprotein mRNA levels," *Inflammation* 11(2):241-251 (1987).
Hartmann et al., "Protein expression profiling reveals distinctive changes in serum proteins associated with chronic pancreatitis," *Pancreas* 35(4):334-342 (2007).
Parker et al., "Reconstituted high-density lipoprotein neutralizes gram-negative bacterial lipopolysaccharides in human whole blood," *Infection and Immunity* 63(1):253-258 (1995).
Piquer et al., "Altered lipid, apolipoprotein, and lipoprotein profiles in inflammatory bowel disease: consequences on the cholesterol efflux capacity of serum using Fu5AH cell system," *Metabolism Clinical and Experimental* 55:980-988 (2006).
Ribeiro et al., "Apolipoprotein AII has an anti-inflammatory effect," *Inflammation Research* vol. 50, Supplement 3: S175, Abstract W13/02 (Sep. 2001).
Sammalkorpi et al., "Changes in serum lipoprotein pattern induced by acute infections," *Metabolism* 37(9):859-865 (1988).
Shen and Howlett, "Alteration in rat apolipoprotein C-III gene expression and lipoprotein composition during inflammation," *Inflammation* 17(2):153-166 (1993).
Vaisar et al., "Myeloperoxidase and inflammatory proteins: pathways for generating dysfunctional high-density lipoprotein in humans," *Curr. Atheroscler. Rep.* 9:417-424 (2007).
Vaisar et al., "Shotgun proteomics implicates protease inhibition and complement activation in the antiinflammatory properties of HDL," *J. Clin. Invest.* 117(3):746-756 (2007).
Wait et al., "Reference maps of mouse serum acute-phase proteins: changes with LPS-induced inflammation and apolipoprotein A-I and A-II transgenes," *Proteomics* 5:4245-4253 (2005).
Watanabe et al., "Hemoglobin and its scavenger protein haptoglobin associate with apoA-1-containing particles and influence the inflammatory properties and function of high density lipoprotein," *J. Biol. Chem.* 284(27):18292-18301 (2009).
Wu et al., "High-density lipoproteins in sepsis and septic shock: metabolism, actions, and therapeutic applications," *Shock* 21(3):210-221 (2004).

* cited by examiner

*Primary Examiner* — Shulamith H Shafer
(74) *Attorney, Agent, or Firm* — Clark & Elbing LLP

(57) ABSTRACT

The invention features methods of using serum factors such as Apolipoprotein A2 and Apolipoprotein C3 for reducing or preventing a chronic or acute inflammatory response (e.g., an inflammatory response due to an autoimmune disease or an injury).

6 Claims, 3 Drawing Sheets

USE OF APOLIPOPROTEINS TO DECREASE INFLAMMATION

CROSS-REFERENCE TO RELATED APPLICATIONS

This application is a U.S. National Stage Application of International Patent Application No. PCT/US2009/047341, filed Jun. 15, 2009, which claims the benefit of U.S. Provisional Patent Application No. 61/131,901, filed Jun. 13, 2008.

STATEMENT AS TO FEDERALLY FUNDED RESEARCH

The invention was made, in part, with government funding provided for by Grant Numbers 5R01GM059694 and 5R01AI059010 awarded by the National Institutes of Health. The federal government has certain rights in the invention.

BACKGROUND OF THE INVENTION

The invention relates to methods of using serum factors having inflammation-inhibitory activity, for example, for reducing a chronic or acute inflammatory response (e.g., an inflammatory response due to an autoimmune disease or an injury).

Chronic inflammation, such as present in autoimmune diseases, is a serious problem. An estimated 2.1 million people in the United States are affected by rheumatoid arthritis, and an estimated one million are affected by inflammatory bowel disease. In addition, acute inflammation such as inflammation due to injury is prevalent in all age groups.

Thus there is a need for identification of treatments that inhibit an inflammatory response.

SUMMARY OF THE INVENTION

We discovered that Apolipoprotein A2 and Apolipoprotein C3, alone, in combination, or in combination with one or more additional apolipoproteins, are involved in regulating the inflammatory response in mammals.

Accordingly, in the first aspect, the invention features a method of reducing or preventing a chronic inflammatory response in a mammal, where the chronic inflammatory response does not involve atherosclerosis. This method involves administering to the mammal a polypeptide including an apolipoprotein A2 amino acid sequence in an amount sufficient to reduce or prevent the chronic inflammatory response. In a desirable embodiment of the first aspect of the invention, the method further involves administering to the mammal a polypeptide including an apolipoprotein C3 amino acid sequence.

The second aspect of the invention features another method of reducing or preventing a chronic inflammatory response in a mammal, where the chronic inflammatory response does not involve atherosclerosis. This method involves administering to the mammal an apolipoprotein C3 amino acid sequence in an amount sufficient to reduce or prevent the chronic inflammatory response. In a desirable embodiment of the second aspect of the invention, the method further involves administering to the mammal a polypeptide including an apolipoprotein A2 amino acid sequence.

In another desirable embodiment of the first and second aspects of the invention, the polypeptide is a recombinant polypeptide.

In additional desirable embodiments of the first aspect of the invention, the apolipoprotein A2 amino acid sequence is a human or a murine apolipoprotein A2 amino acid sequence and in additional desirable embodiments of the second aspect of the invention, the apolipoprotein C3 amino acid sequence is a human or murine apolipoprotein C3 amino acid sequence.

In other desirable embodiments of the first and second aspects of the invention, the chronic inflammatory response is from an autoimmune disease. Desirably, the autoimmune disease is rheumatoid arthritis, inflammatory bowel disease, or psoriasis. In yet another desirable embodiment of the first and second aspects of the invention, the chronic inflammatory response includes activation of macrophages.

In the third aspect, the invention features a method of reducing or preventing an acute inflammatory response in a mammal, where the acute inflammatory response does not involve sepsis. The method involves administering to the mammal a polypeptide including an apolipoprotein A2 amino acid sequence in an amount sufficient to reduce or prevent the acute inflammatory response. In a desirable embodiment of the third aspect of the invention, the method further involves administering to the mammal a polypeptide including an apolipoprotein C3 amino acid sequence.

In the fourth aspect, the invention features another method of reducing or preventing an acute inflammatory response in a mammal, where the acute inflammatory response does not involve sepsis. This method involves administering to the mammal a polypeptide including an apolipoprotein C3 amino acid sequence in an amount sufficient to reduce or prevent the acute inflammatory response. In a desirable embodiment of the fourth aspect of the invention, the method further involves administering to the mammal a polypeptide including an apolipoprotein A2 amino acid sequence.

In additional desirable embodiments of the third and fourth aspects of the invention, the inflammatory response is from an injury (e.g., a burn), ileus (e.g., post surgical ileus), acute respiratory distress syndrome (ARDS), ischemic reperfusion injury, pancreatitis, or a gastric or coronary bypass related illness.

In further desirable embodiments of any of the aspects of the invention, the mammal is a human. In other desirable embodiments of any of the aspects of the invention, the polypeptide is a human polypeptide.

DEFINITIONS

By "apolipoprotein A2 amino acid sequence" or "apoA2 amino acid sequence" as used herein is meant a polypeptide that is substantially identical over its full length to the amino acid sequence of GenBank Accession No. CAA44616 (*Mus musculus*), NP_038502 (*Mus musculus*), ABV02576 (*Mus musculus*), CAH72151 (*Homo sapiens*), BAD 05173 (*Homo sapiens*), AAM49807 (*Homo sapiens*), NP_001008976 (*Pan troglodytes*), AAM49808 (*Pan troglodytes*), NP_037244 (*Rattus norvegicus*), NP_001039381 (*Bos taurus*), or P02653 (*Macaca mulatta*), or a fragment thereof, and that can reduce or prevent a chronic or acute inflammatory response in a mammal. Desirably, an "apolipoprotein A2 amino acid sequence" or "apoA2 amino acid sequence" is identical to the amino acid sequence of CAA44616, NP_038502, ABV02576, CAH72151, BAD05173, AAM49807, NP_001008976, AAM49808, NP_037244, NP_001039381, or P02653 over its full length. Assays for determining whether an "apolipoprotein A2 amino acid sequence" or "apoA2 amino acid sequence" can reduce or prevent a chronic or acute inflammatory response in a mammal are described herein and include, for example, cell culture assays using, for example, macrophages. In desirable embodiments, the apolipoprotein A2 amino acid sequence is a recombinant polypeptide (i.e., a polypeptide produced from a recombinant nucleic acid sequence). Recombinant apolipoprotein A2 can be expressed, for example, in bacterial cells (e.g., *E. coli*) using standard techniques.

By "apolipoprotein C3 amino acid sequence" or "apoC3 amino acid sequence" as used herein is meant a polypeptide that is substantially identical over its full length to the amino acid sequence of GenBank Accession No. NP_075603 (*Mus musculus*), AAB59372 (*Homo sapiens*), NP_036633 (*Rattus norvegicus*), NP_011002801 (*Sus scrofa*), or BAD 15291 (*Bos taurus*), or a fragment thereof, and that can reduce or prevent a chronic or acute inflammatory response in a mammal. Desirably, an "apolipoprotein C3 amino acid sequence" or "apoC3 amino acid sequence" is identical to the amino acid sequence of NP_075603, AAB59372, NP_036633, NP_011002801, or BAD15291 over its full length. Assays for determining whether an "apolipoprotein C3 amino acid sequence" or "apoC3 amino acid sequence" can reduce or prevent a chronic or acute inflammatory response in a mammal are described herein and include, for example, cell culture assays using, for example, macrophages. In desirable embodiments, the apolipoprotein C3 amino acid sequence is a recombinant polypeptide (i.e., a polypeptide produced from a recombinant nucleic acid sequence). Recombinant apolipoprotein C3 can be expressed, for example, in bacterial cells (e.g., *E. coli*) using standard techniques.

By "cytokine response" is meant an increase in expression or activity of a cytokine in a subject or in cell culture. Desirably, the cytokine response does not involve sepsis. In other desirable embodiments, the cytokine response involves induction or activation of Tumor Necrosis Factor α (TNFα), IL-6, IL-8, or IL-10. Desirably, a cytokine response also involves p38 MAP kinase, erk1/2, or NF-κB activation.

By "chronic inflammatory response" is meant the prolonged activation of the immune system in a subject. Atherosclerosis is specifically excluded from the definition of a chronic inflammatory response. The activation of the immune system desirably is at least 3 months, 6 months, 1 year, 5 years, 10 years, or even life-long. Desirably the subject is a mammal such as a human. A chronic inflammatory response preferably involves the induction of cytokines and may result from an autoimmune disease such as rheumatoid arthritis, psoriasis, or inflammatory bowel disease. In a desirable embodiment, the chronic inflammatory response requires the activation of macrophages.

By "acute inflammatory response" is meant a short-term activation of the immune system in a subject, where the inflammatory response does not involve sepsis. The short-term activation of the immune response in the subject desirably is present for less than one month, for example, less than two weeks, less than one week, less than one day, less than 12 hours, or even less than 6 hours. Desirably, the acute inflammatory response results from an injury such as a burn, trauma, ARDS (acute respiratory distress syndrome), ileus such as post surgical ileus, ischemic reperfusion injury, post bypass (e.g., coronary or gastric bypass) related illnesses, or pancreatitis. In a desirable embodiment, the acute inflammatory response requires the activation of macrophages.

By "sepsis" is meant inflammation in the setting of an infection.

By an "autoimmune disease" is meant an immune response against a self-antigen that results in inflammation or destruction of healthy tissue in a subject. Desirably the subject is a mammal, such as a human. Exemplary autoimmune diseases include, but are not limited to, arthritis (e.g., rheumatoid arthritis such as acute arthritis, chronic rheumatoid arthritis, gouty arthritis, acute gouty arthritis, chronic inflammatory arthritis, degenerative arthritis, infectious arthritis, Lyme arthritis, proliferative arthritis, psoriatic arthritis, vertebral arthritis, and juvenile-onset rheumatoid arthritis, osteoarthritis, arthritis chronica progrediente, arthritis deformans, polyarthritis chronica primaria, reactive arthritis, and ankylosing spondylitis), inflammatory hyperproliferative skin diseases, psoriasis such as plaque psoriasis, gutatte psoriasis, pustular psoriasis, and psoriasis of the nails, dermatitis including contact dermatitis, chronic contact dermatitis, allergic dermatitis, allergic contact dermatitis, dermatitis herpetiformis, and atopic dermatitis, x-linked hyper IgM syndrome, urticaria such as chronic allergic urticaria and chronic idiopathic urticaria, including chronic autoimmune urticaria, polymyositis/dermatomyositis, juvenile dermatomyositis, toxic epidermal necrolysis, scleroderma (including systemic scleroderma), sclerosis such as systemic sclerosis, multiple sclerosis (MS) such as spino-optical MS, primary progressive MS (PPMS), and relapsing remitting MS (RRMS), progressive systemic sclerosis, sclerosis disseminata, and ataxic sclerosis, inflammatory bowel disease (IBD) (for example, Crohn's disease, autoimmune-mediated gastrointestinal diseases, colitis such as ulcerative colitis, colitis ulcerosa, microscopic colitis, collagenous colitis, colitis polyposa, necrotizing enterocolitis, and transmural colitis, and autoimmune inflammatory bowel disease), pyoderma gangrenosum, erythema nodosum, primary sclerosing cholangitis, episcleritis, respiratory distress syndrome, including adult or acute respiratory distress syndrome (ARDS), meningitis, inflammation of all or part of the uvea, iritis, choroiditis, an autoimmune hematological disorder, rheumatoid spondylitis, sudden hearing loss, IgE-mediated diseases such as anaphylaxis and allergic and atopic rhinitis, encephalitis such as Rasmussen's encephalitis and limbic and/or brainstem encephalitis, uveitis, such as anterior uveitis, acute anterior uveitis, granulomatous uveitis, non-granulomatous uveitis, phacoantigenic uveitis, posterior uveitis, or autoimmune uveitis, glomerulonephritis (GN) with and without nephrotic syndrome such as chronic or acute glomerulonephritis such as primary GN, immune-mediated GN, membranous GN (membranous nephropathy), idiopathic membranous GN or idiopathic membranous nephropathy, membrano- or membranous proliferative GN (MPGN), including Type I and Type II, and rapidly progressive GN, allergic conditions, allergic reaction, eczema including allergic or atopic eczema, asthma such as asthma bronchiale, bronchial asthma, and auto-immune asthma, conditions involving infiltration of T cells and chronic inflammatory responses, chronic pulmonary inflammatory disease, autoimmune myocarditis, leukocyte adhesion deficiency, systemic lupus erythematosus (SLE) or systemic lupus erythematodes such as cutaneous SLE, subacute cutaneous lupus erythematosus, neonatal lupus syndrome (NLE), lupus erythematosus disseminatus, lupus (including nephritis, cerebritis, pediatric, non-renal, extra-renal, discoid, alopecia), juvenile onset (Type I) diabetes mellitus, including pediatric insulin-dependent diabetes mellitus (IDDM), adult onset diabetes mellitus (Type II diabetes), autoimmune diabetes, idiopathic diabetes insipidus, immune responses associated with acute and delayed hypersensitivity mediated by cytokines and T-lymphocytes, tuberculosis, sarcoidosis, granulomatosis including lymphomatoid granulomatosis, Wegener's granulomatosis, agranulocytosis, vasculitides, including vasculitis (including large vessel vasculitis (including polymyalgia rheumatica and giant cell (Takayasu's) arteritis), medium vessel vasculitis (including Kawasaki's disease and polyarteritis nodosa), microscopic polyarteritis, CNS vasculitis, necrotizing, cutaneous, or hypersensitivity vasculitis, systemic necrotizing vasculitis, and ANCA-associated vasculitis, such as Churg-Strauss vasculitis or syndrome (CSS)), temporal arteritis, aplastic anemia, autoimmune aplastic anemia, Coombs positive anemia, Diamond Blackfan anemia, hemolytic anemia or immune hemolytic anemia including autoimmune hemolytic anemia (AIHA), pernicious anemia (anemia perniciosa), Addison's disease, pure red cell anemia or aplasia (PRCA), Factor VIII deficiency, hemophilia A, autoimmune neutropenia, pancytopenia, leukopenia, diseases involving leukocyte diapedesis, CNS inflammatory disorders, multiple organ injury syndrome such as those secondary to septicemia, trauma or hemorrhage, antigen-antibody complex-mediated diseases, antiglomerular basement membrane disease, anti-phospholipid antibody syndrome, allergic neuritis, Bechet's or Behcet's disease, Castleman's syndrome, Goodpasture's syndrome, Reynaud's syndrome, Sjogren's syndrome, Stevens-Johnson syndrome, pemphigoid such as pemphigoid bullous and skin pemphigoid, pemphigus (including pemphigus vulgaris, pemphigus foliaceus, pemphigus mucus-membrane pemphigoid, and pemphigus erythematosus), autoimmune polyendocrinopathies, Reiter's disease or syndrome, immune complex nephritis, antibody-mediated nephritis, neuromyelitis optica, polyneuropathies, chronic neuropathy such as IgM polyneuropathies or IgM-mediated neuropathy, thrombocytopenia (as developed by myocardial infarction patients, for example), including thrombotic thrombocytopenic purpura (TTP) and autoimmune or immune-mediated thrombocytopenia such as idiopathic thrombocytopenic purpura (ITP) including chronic or acute ITP, autoimmune disease of the testis and ovary including autoimmune orchitis and oophoritis, primary hypothyroidism, hypoparathyroidism, autoimmune endocrine diseases including thyroiditis such as autoimmune thyroiditis, Hashimoto's disease, chronic thyroiditis (Hashimoto's thyroiditis), or subacute thyroiditis, autoimmune thyroid disease, idiopathic hypothyroidism, Grave's disease, polyglandular syndromes such as autoimmune polyglandular syndromes (or polyglandular endocrinopathy syndromes), paraneoplastic syndromes, including neurologic paraneoplastic syndromes such as Lambert-Eaton myasthenic syndrome or Eaton-Lambert syndrome, stiff-man or stiff-person syndrome, encephalomyelitis such as allergic encephalomyelitis or encephalomyelitis allergica and experimental allergic encephalomyelitis (EAE), myasthenia gravis such as thymoma-associated myasthenia gravis, cerebellar degeneration, neuromyotonia, opsoclonus or opsoclonus myoclonus syndrome (OMS), and sensory neuropathy, multifocal motor neuropathy, Sheehan's syndrome, autoimmune hepatitis, chronic hepatitis, lupoid hepatitis, giant cell hepatitis, chronic active hepatitis or autoimmune chronic active hepatitis, lymphoid interstitial pneumonitis, bronchiolitis obliterans (non-transplant) vs NSIP, Guillain-Barré syndrome, Berger's disease (IgA nephropathy), idiopathic IgA nephropathy, linear IgA dermatosis, primary biliary cirrhosis, pneumonocirrhosis, autoimmune enteropathy syndrome, Celiac disease, Coeliac disease, celiac sprue (gluten enteropathy), refractory sprue, idiopathic sprue, cryoglobulinemia, amylotrophic lateral sclerosis (ALS; Lou Gehrig's disease), coronary artery disease, autoimmune ear disease such as autoimmune inner ear disease (AIED), autoimmune hearing loss, opsoclonus myoclonus syndrome (OMS), polychondritis such as refractory or relapsed polychondritis, pulmonary alveolar proteinosis, amyloidosis, scleritis, a non-cancerous lymphocytosis, a primary lymphocytosis, which includes monoclonal B cell lymphocytosis (e.g., benign monoclonal gammopathy and monoclonal garnmopathy of undetermined significance, MGUS), peripheral neuropathy, paraneoplastic syndrome, channelopathies such as epilepsy, migraine, arrhythmia, muscular disorders, deafness, blindness, periodic paralysis, and channelopathies of the CNS, autism, inflammatory myopathy, focal segmental glomerulosclerosis (FSGS), endocrine ophthalmopathy, uveoretinitis, chorioretinitis, autoimmune hepatological disorder, fibromyalgia, multiple endocrine failure, Schmidt's syndrome, adrenalitis, gastric atrophy, presenile dementia, demyelinating diseases such as autoimmune demyelinating diseases, diabetic nephropathy, Dressler's syndrome, alopecia areata, CREST syndrome (calcinosis, Raynaud's phenomenon, esophageal dysmotility, sclerodactyly, and telangiectasia), male and female autoimmune infertility, mixed connective tissue disease, Chagas' disease, rheumatic fever, recurrent abortion, farmer's lung, erythema multiforme, post-cardiotomy syndrome, Cushing's syndrome, bird-fancier's lung, allergic granulomatous angiitis, benign lymphocytic angiitis, Alport's syndrome, alveolitis such as allergic alveolitis and fibrosing alveolitis, interstitial lung disease, transfusion reaction, leprosy, malaria, leishmaniasis, kypanosomiasis, schistosomiasis, ascariasis, aspergillosis, Sampter's syndrome, Caplan's syndrome, dengue, endocarditis, endomyocardial fibrosis, diffuse interstitial pulmonary fibrosis, interstitial lung fibrosis, idiopathic pulmonary fibrosis, cystic fibrosis, endophthalmitis, erythema elevatum et diutinum, erythroblastosis fetalis, eosinophilic faciitis, Shulman's syndrome, Felty's syndrome, flariasis, cyclitis such as chronic cyclitis, heterochronic cyclitis, iridocyclitis, or Fuch's cyclitis, Henoch-Schonlein purpura, human immunodeficiency virus (HIV) infection, echovirus infection, cardiomyopathy, Alzheimer's disease, parvovirus infection, rubella virus infection, post-vaccination syndromes, congenital rubella infection, Epstein-Barr virus infection, mumps, Evan's syndrome, autoimmune gonadal failure, Sydenham's chorea, post-streptococcal nephritis, thromboangitis ubiterans, thyrotoxicosis, tabes dorsalis, choriooiditis, giant cell polymyalgia, endocrine ophthamopathy, chronic hypersensitivity pneumonitis, keratoconjunctivitis sicca, epidemic keratoconjunctivitis, idiopathic nephritic syndrome, minimal change nephropathy, benign familial and ischemia-reperfusion injury, retinal autoimmunity, joint inflammation, bronchitis, chronic obstructive airway disease, silicosis, aphthae, aphthous stomatitis, arteriosclerotic disorders, aspermiogenese, autoimmune hemolysis, Boeck's disease, cryoglobulinemia, Dupuytren's contracture, endophthalmia phacoanaphylactica, enteritis allergica, erythema nodosum leprosum, idiopathic facial paralysis, chronic fatigue syndrome, febris rheumatica, Hamman-Rich's disease, sensoneural hearing loss, haemoglobinuria paroxysmatica, hypogonadism, ileitis regionalis, leucopenia, mononucleosis infectiosa, traverse myelitis, primary idiopathic myxedema, nephrosis, ophthalmia symphatica, orchitis granulomatosa, pancreatitis, polyradiculitis acuta, pyoderma gangrenosum, Quervain's thyreoiditis, acquired spenic atrophy, infertility due to anti-spermatozoan antibodies, non-malignant thymoma, vitiligo, SCID and Epstein-Barr virus-associated diseases, acquired immune deficiency syndrome (AIDS), parasitic diseases such as *Leishmania*, toxic-shock syndrome, food poisoning, conditions involving infiltration of T cells, leukocyte-adhesion deficiency, immune responses associated with acute and delayed hypersensitivity mediated by cytokines and T-lymphocytes, diseases involving leukocyte diapedesis, multiple organ injury syndrome, antigen-antibody complex-mediated diseases, antiglomerular basement membrane disease, allergic neuritis, autoimmune polyendocrinopathies, oophoritis, primary myxedema, autoimmune atrophic gastritis, sympathetic ophthalmia, rheumatic diseases, mixed connective tissue disease, nephrotic syndrome, insulitis, polyendocrine failure, peripheral neuropathy, autoimmune polyglandular syndrome type I, adult-onset idiopathic hypoparathyroidism (AOIH), alopecia totalis, dilated cardiomyopathy, epidermolisis bullosa acquisita (EBA), hemochromatosis, myocarditis, nephrotic syndrome, primary sclerosing cholangitis, purulent or nonpurulent sinusitis, acute or chronic sinusitis, ethmoid, frontal, maxillary, or sphenoid sinusitis, an eosinophil-related disorder such as eosinophilia, pulmonary infiltration eosinophilia, eosinophilia-myalgia syndrome, Loffler's syndrome, chronic eosinophilic pneumonia, tropical pulmonary eosinophilia, bronchopneumonic aspergillosis, aspergilloma, or granulomas containing eosinophils, anaphylaxis, seronegative spondyloarthritides, polyendocrine autoimmune disease, sclerosing cholangitis, sclera, episclera, chronic mucocutaneous candidiasis, Bruton's syndrome, transient hypogammaglobulinemia of infancy, Wiskott-Aldrich syndrome, ataxia telangiectasia, autoimmune disorders associated with collagen disease, rheumatism, neurological disease, ischemic re-perfusion disorder, reduction in blood pressure response, vascular dysfunction, antgiectasis, tissue injury, cardiovascular ischemia, hyperalgesia, cerebral ischemia, and disease accompanying vascularization, allergic hypersensitivity disorders, glomerulonephritides, reperfusion injury, reperfusion injury of myocardial or other tissues, dermatoses with acute inflammatory components, acute purulent meningitis or other central nervous system inflammatory disorders, ocular and orbital inflammatory disorders, granulocyte transfusion-associated syndromes, cytokine-induced toxicity, acute serious inflammation, chronic intractable inflammation, pyelitis, pneumonocirrhosis, diabetic retinopathy, diabetic large-artery disorder, endarterial hyperplasia, peptic ulcer, valvulitis, and endometriosis. Desirably, an autoimmune disease is rheumatoid arthritis, psoriasis, or inflammatory bowel disease.

By "purified" is meant separated from other components that naturally accompany it. Typically, a compound is substantially pure when it is at least 50%, by weight, free from proteins, antibodies, and naturally-occurring organic molecules with which it is naturally associated. Preferably, the compound is at least 75%, more preferably, at least 90%, and most preferably, at least 99%, by weight, pure. A substantially pure compound may be obtained by chemical synthesis, separation of the factor from natural sources, or production of the factor in a recombinant host cell that does not naturally produce the factor. Desirably, the compound is purified from serum or from HDL. A compound, for example, a protein, may be purified by one skilled in the art using standard techniques, such as those described by Ausubel et al. (Current Protocols in Molecular Biology, John Wiley & Sons, New York, 2000). The compound is preferably at least 2, 5, or 10-times as pure as the starting material, as measured using polyacrylamide gel electrophoresis, column chromatography, optical density, HPLC (high pressure liquid chromatography) analysis, or Western analysis (Ausubel et al. Current Protocols in Molecular Biology, John Wiley & Sons, New York, 2000). Preferred methods of purification include salt precipitation, gel filtration, hydrophobic interaction chromatography, ion exchange chromatography, lectin chromatography, reversed phase chromatography, chromatofocusing, as well as combinations of these methods.

By a compound that "decreases a cytokine response" is meant a compound that decreases protein or nucleic acid level or activity of a cytokine in a cell, a cell extract, or a cell supernatant. For example, such a compound may decrease RNA stability, transcription, translation, or protein degradation. It will be appreciated that the degree of decrease provided by a compound in a given assay will vary, but that one skilled in the art can determine the statistically significant change (e.g., a p-value $\leq 0.05$) in the level of the specific protein or nucleic acid affected by a compound. In desirable embodiments, the expression or activity of Tumor Necrosis Factor $\alpha$, IL-6, or IL-8 is decreased. In further desirable embodiments a compound that decreases a cytokine response activates p38 MAP kinase, erk1/2, or NF-κB.

By a "compound," "candidate compound," or "factor" is meant a chemical, be it naturally-occurring or artificially-derived. Compounds may include, for example, peptides, polypeptides, synthetic organic molecules, naturally-occurring organic molecules, nucleic acid molecules, and components or combinations thereof.

By a "protein" is meant two or more amino acids joined by a peptide bond. Proteins of the invention may exist as monomers, dimers, or other oligomers.

By "substantially identical" is meant a polypeptide or nucleic acid sequence exhibiting at least 50%, preferably 60%, 70%, 75%, or 80%, more preferably 85%, 90% or 95%, and most preferably 99% identity to a reference amino acid or nucleic acid sequence. For polypeptides, the length of comparison sequences will generally be at least 15 contiguous amino acids, preferably at least 20 contiguous amino acids, more preferably at least 25, 50, 75, 90, 100, 150, 200, 250, or 300 contiguous amino acids, and most preferably the full-length amino acid sequence. For nucleic acids, the length of comparison sequences will generally be at least 45 contiguous nucleotides, preferably at least 60 contiguous nucleotides, more preferably at least 75, 150, 250, 300, 450, 600, 750, or 900 contiguous nucleotides, and most preferably the full-length nucleotide sequence.

Sequence identity is typically measured using sequence analysis software with the default parameters specified therein (e.g., Sequence Analysis Software Package of the Genetics Computer Group, University of Wisconsin Biotechnology Center, 1710 University Avenue, Madison, Wis. 53705). This software program matches similar sequences by assigning degrees of homology to various substitutions, deletions, and other modifications.

Substantially identical nucleic acid sequences also include nucleic acid sequences that hybridize to the complement of a given nucleic acid sequence under high stringency hybridization conditions. Exemplary high stringency hybridization conditions include hybridization at approximately 42° C. in about 50% formamide, 0.1 mg/ml sheared salmon sperm DNA, 1% SDS (Sodium Dodecyl Sulfate), 2×SSC (Sodium Citrate Buffer), 10% Dextran Sulfate, a first wash at approximately 65° C. in about 2×SSC, 1% SDS, followed by a second wash at approximately 65° C. in about 0.1×SSC. Alternatively, high stringency hybridization conditions may include hybridization at approximately 42° C. in about 50% formamide, 0.1 mg/ml sheared salmon sperm DNA, 0.5% SDS, 5× SSPE, 1× Denhardt's, followed by two washes at room temperature in 2×SSC, 0.1% SDS, and two washes at between 55-60° C. in 0.2×SSC, 0.1% SDS.

Other features and advantages of the invention will be apparent from the following Detailed Description, the Drawings, and the Claims.

DETAILED DESCRIPTION

The present invention is a further development from our discovery that serum factors are involved in the regulation of an inflammatory response (see, e.g., WO 2007/111938, the disclosure of which is hereby incorporated by reference). The initial discovery was made by comparing the inflammatory response to LPS in the presence of serum from species that exhibit differences in their LPS sensitivity. As a marker for the inflammatory response, cytokine expression, e.g., TNF or IL-6 levels, were measured in cell supernatants after stimulation with LPS. In addition, a correlation between in vitro cytokine production and in vivo LPS sensitivity, represented by the LD50 dose (mg/kg), was investigated for various species, and it was determined that serum factors played an important role in LPS sensitivity. We now determined, after further characterization, that many of the serum factors are high density lipoproteins (HDL). As such, due to the difficulty in separating some of these proteins from each other, we purified HDL first, removed the lipid, and further purified the apolipoproteins. This approach yielded two to three peaks on a mass spectroscopy column. As described herein, one of the peaks that contained the highest activity in decreasing TNF production from macrophages contains Apolipoprotein A2 and Apolipoprotein C3. In view of our data, Apolipoprotein A2 and Apolipoprotein C3, alone, in combination, or in combination with one or more additional apolipoproteins, likely can be used to treat or reduce the risk of acquiring a chronic or acute inflammatory response resulting in a disorder in a mammal, such as a human.

The following examples are meant to illustrate the invention and should not be construed as limiting.

Example 1

Identification of Apolipoproteins A2 and C3 as TNF-Inhibiting Serum Factors

Figure 1:
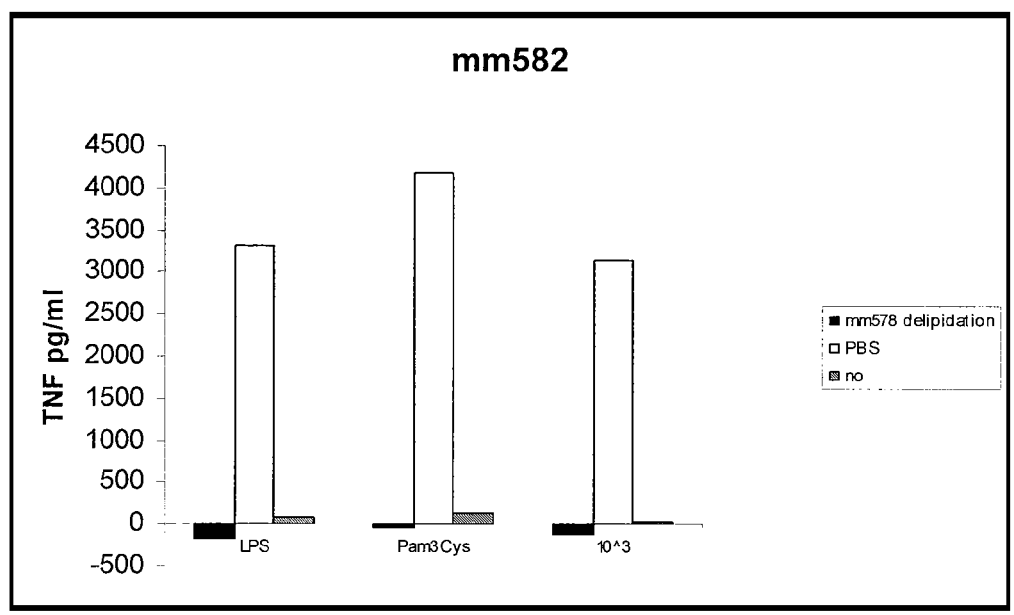
FIG. 1 is a graph showing the effect on TNF (tumor necrosis factor) induction of total delipidated mouse high density lipoprotein (HDL) incubated with macrophages in presence of lipopolysaccharide (LPS), a TLR2 (Toll-like receptor 2) agonist (Pam3Cys) or killed *E. coli* bacteria (10e3). Culture supernatants were assayed for TNF after 18 hours.
Figure 2:
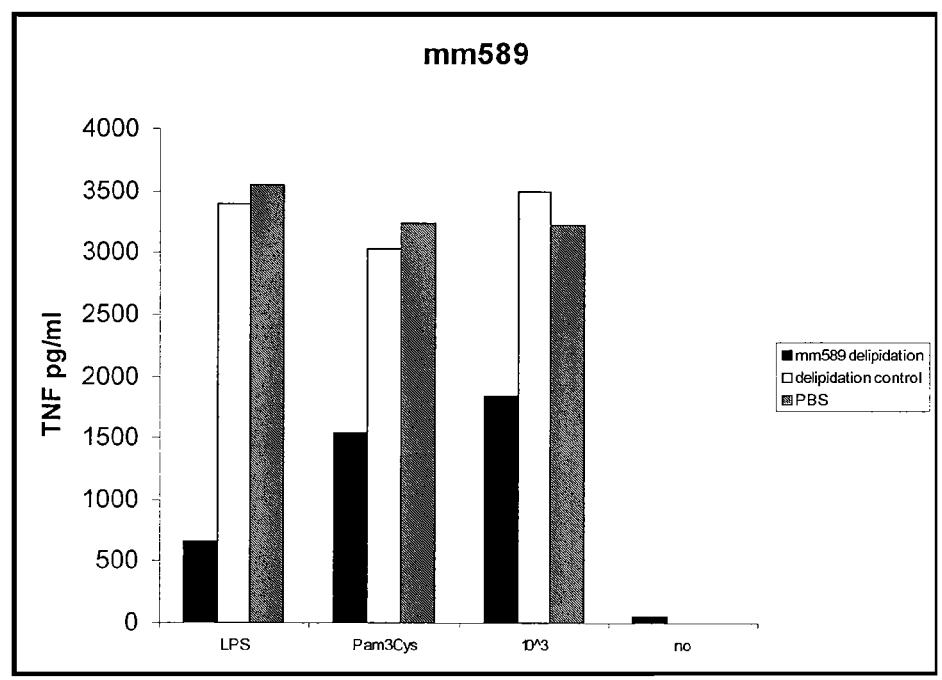
FIG. 2 is another graph showing the effect on TNF induction of total delipidated mouse HDL with a less marked effect than shown in FIG. 1. The delipidation control was PBS (phosphate buffered saline) that, in parallel, was carried through the same delipidation and dialysis procedures.
Figure 3:
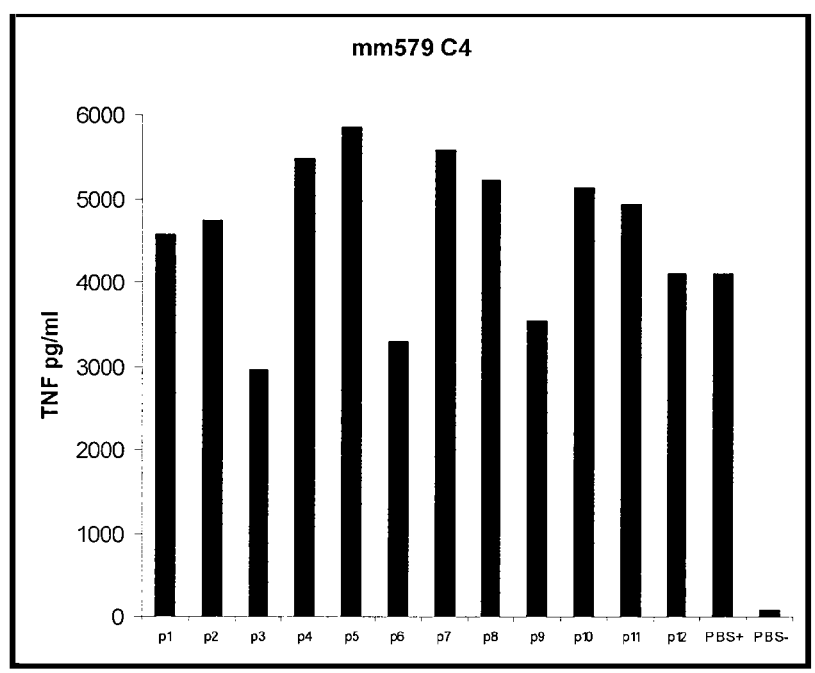
FIG. 3 is a graph showing the results of testing the C4 reverse phase HPLC (high pressure liquid chromatography) column fractions of the total delipidated mouse HDL for their ability to inhibit LPS-induced induction of TNF from bone marrow derived macrophages.

As shown in FIG. 1, total delipidated mouse HDL completely inhibited LPS-mediated induction of TNF in macrophages. In particular, total delipidated mouse HDL was incubated with macrophages in the presence of LPS, a TLR2 (Toll-like receptor 2) agonist (Pam3Cys), or killed E. coli bacteria (10e3). The culture supernatants were assayed for the presence of TNF after 18 hours. These experiments were repeated and a similar, although less-marked effect was observed (FIG. 2). Total delipidated mouse HDL was then fractionated on a C4 reverse phase HPLC (high pressure liquid chromatography) column. The fractions were tested for activity in the TNF-induction bone marrow derived macrophage assay as described herein. Three peaks of activity were identified (FIG. 3). Protein analysis of fraction p6, the middle peak, by mass spectroscopy indicated that this peak contains Apolipoprotein A2 and Apolipoprotein C3.

Example 2

Purification of Apolipoprotein A2 and C3

To purify Apolipoprotein A2 and Apolipoprotein C3, twelve milliliters of mouse serum were adjusted to a median density of 1.21 g/ml with KBr, and centrifuged (2 ml each tube) at 48,700 rpm in a Beckman SwrrTi rotor (250,000×g) at 4° C. for 42 hours. The top thirds of the centrifuge tubes were collected and washed by a repeat centrifugation using identical conditions for 65 hours. The top third of the washed material was transferred to new tubes and adjusted to a density of 1.063 g/ml with KBr. This material was centrifuged at 48,700 rpm (250,000×g) for 42 hours. The bottom third of this tube was collected after centrifugation and dialyzed against PBS for 48 hours. This material was delipidated with chloroform/methanol as described by Brewer, Jr. et al. ("Isolation and Characterization of Apolipoproteins A-I, A-II, and A-IV," Methods in Enzymology 128:223-246, 1986). Briefly, 3 mls of the collected material above were mixed with same volume of chloroform:methanol (2:1, V/V) and intermittent vortexing for 1 hour at 4° C. The sample was centrifuged at 2000 rpm for 15 minutes at 5° C. The top of material in the tube was saved and this same extraction was repeated 4 times. Following this procedure the material was dialyzed against water for 64 hours. This material (protein concentration 20 µg/ml) was found to potently inhibit the production of tumor necrosis factor (TNF) from mouse bone marrow derived macrophages (BMDMs) when stimulated by LPS (a TLR4 (Toll-like receptor 4) agonist), Pam-3-Cys (a synthetic peptide TLR2 agonist), and killed E. coli bacteria. Fifty micrograms of this material was injected onto a C4 reverse phase high pressure liquid chromatography column, and fractions from the resultant material were split and analyzed for the ability to decrease LPS-induced TNF from mouse bone marrow derived macrophages. The macrophage assay is described in more detail in Example 3. A fraction with high potency for decreasing LPS-induced TNF production (p6; FIG. 3) was split and analyzed by mass spectroscopy. This analysis revealed Apolipoprotein A2 and Apolipoprotein C3.

Example 3

Materials and Methods

The experiments described herein may be carried out using the following materials and methods.

Macrophage Assay

The macrophage assay has been optimized and streamlined for high sensitivity, small volumes, and rapid turnover of results. Any type of macrophage (e.g., mouse bone marrow-derived macrophages) may be used for this assay. The cells can be prepared in large numbers, frozen in aliquots and have less day-to-day variation than the RAW cell line. The cells can be prepared and stimulated with a fixed concentration of LPS on a sensitive portion of the dose response curve in the presence of separated fractions of mouse serum. LPS is used simply to activate macrophages for the assay and the results obtained using LPS-activated macrophages are indicative of results expected for activated macrophages in general. Fractions can be added to pre-prepared and slightly concentrated media to prevent dilution. Supernatants can be tested by ELISA for TNF (or IL-1β, IL-6, or IL-10) and compared and fractions that suppress the production of TNF (or IL-1β, IL-6, or IL-10) can be pooled for subsequent purification. Routine controls for the assay may include no LPS, LPS with no added fractions, and starting material with known suppressing activity. Results may be verified with a full dilution series of LPS, and with dilutions of active suppressing fractions to provide better measurements of the potency of the factor. To ensure that the compound purified from mouse serum reproduces the results observed with whole serum, active fractions may be tested to ensure that they suppress IL-6 production. Similarly, the active fractions may be tested for cytokine suppression using other stimuli, e.g., killed whole bacterial cells or the Pam-3-Cys synthetic peptide, to eliminate the possibility that the purified compound binds and neutralizes LPS, rather than acting at the cellular level. Activation of mouse or human macrophages by LPS may require LPS binding protein (LBP) for optimal signaling. If insufficient TNF is induced from the cells by the added LPS, small amounts of fetal calf serum or purified LBP (Biometec, Greifswald, Germany) may be added as a source of LBP. However, good activation of both mouse and human cells signaling is observed without serum or exogenous LBP, using either LPS or other PAMPs (pathogen-associated molecular patterns). Thus, it is not desirable to add LBP, as an LBP-dependent signal would not reflect signaling from other PAMPs. Mouse serum from LBP KO mice also suppresses TNF in the assay.

In another embodiment, a PAMP other than LPS may be used (which would not be affected by LBP) to stimulate the cells in the assay. As the factor acts on the cells when pre-incubated, physical interaction of the protein with the stimulant may not be required. In yet another embodiment, the cells may be pre-incubated with the fractions, washed, and then stimulated with LPS to remove LBP from the assay. This may avoid confounding effects of the possible presence LBP in the fractions from the assay.

Macrophage Cells

Mouse Bone Marrow Derived Macrophages

Bone marrow-derived macrophages (BMDMs) were prepared from mice according to the protocol described by Schilling et al. (*J. Immunol.* 169:5874-5880, 2002). These cells can be frozen down in large numbers for use in multiple studies.

Femurs from female C57BL/6 mice were isolated after euthanasia by $CO_2$ asphyxiation. The ends of the femur were cut off, and, to flush out the stem cells, the femurs were washed with RPMI 1640 supplemented with 10% mouse, human or fetal calf serum, 1% HEPES, 1% penicillin/streptomycin (10,000 U/ml), sodium pyruvate (100 mM), 1% non-essential amino acids (10 mM), and 0.5% β-mercapthoethinol, penicillin, and streptomycin (basic BMDM media). Red blood cells were lysed with red blood cell lysis buffer obtained from Sigma. After washing of lysis buffer by spinning, viable cells were counted by staining with trypan blue and reconstituted in basic BMDM media supplemented with 0.50% fetal calf serum, 5% horse serum, 30% M-CSF (conditioned medium from cultures of L929 cells) (Weber et al., *J. Immunol.* 151:415-424, 1993), and 0.5% glucose (Differential media) to a concentration of $5 \times 10^6$ cells/30 ml basic medium supplemented with an additional 5% serum, 1.5 mM glucose, and M-CSF (30% conditioned medium from cultures of L929 cells) (Weber et al., *J. Immunol.* 151:415-424, 1993). Cells were cultured one week at 37° C., 5-10% $CO_2$ in pyrogen free bags (5×30 cm) made of hydrophobic Teflon foil (BioFOLIE, Sartorius).

After culturing, bags were checked for contamination by microscope. Cells were collected by sterile technique into a single pellet and reconstituted in cryoprotective media at $1.5 \times 10^7$ cells/ml and frozen at −80° C. Cells were transferred to liquid nitrogen for 3-7 days. Before stimulating, cells were thawed, reconstituted in basic BMDM media, and plated in a 96-well plate at a density of 400,000 cells/cm², and incubated overnight at 37° C., 5-10% $CO_2$. Alternatively, cells may be incubated for 7 days at 37° C., in 5% $CO_2$, harvested, and placed in wells of 48-well plates at a density of $4-6 \times 10^5/cm^2$ for 24-48 hours in to allow adherence. BMDMs may then be washed and stimulated in media containing either no serum or the same serum that the cells were harvested and cultured in.

Mouse Peritoneal Exudative Macrophages (PEM)

Female C3H/HEN mice (commercially available at Charles River laboratories) can be injected intraperitoneally with 1 mL of sterile 3% brewer's thioglycollate (Call et al., *Am. J. Pathol.* 158:715-721, 2001); 4-5 days later exudate macrophages are harvested. Mice can be euthanized by $CO_2$ asphyxiation and peritoneal macrophages obtained by peritoneal lavage with 10 mL of sterile DMEM culture media. Viable cells can be counted by staining with trypan blue and plated in a 96-well plate at a concentration of $1.28 \times 10^6$ cells/ml DMEM culture media in 100 ml/well. Plates can be cultured at 37° C., 5-10% $CO_2$ for 3-4 hours before being stimulated.

Mouse Peripheral Blood Mononuclear Cells (MPBMCs)

MPBMCs can be prepared by centrifugation using Lympholyte M (Cedarlane, Ontario) according to the manufacturer's directions rather than Ficol. Cells may be counted as above and differential cell numbers determined by staining of aliquots. Purity of cells can be assessed by flow cytometry. Prior to use, media can be replaced with media containing no serum, or mouse, human or fetal calf serum.

RAW264.7 Mouse Macrophage Cell Line (RAW Cells)

RAW cells can be obtained from the American Type Culture Collection (ATCC) and grown as specified by the ATCC. Cells can be maintained in the presence of 10% fetal calf serum or, as above, in autologous serum. Results from cells maintained in fetal calf serum may be compared with those maintained in autologous serum. Cells should not be passaged more that 10 times. Prior to the experiments, serum in the media may be replaced with media containing no serum, mouse serum, human serum, or fetal calf serum.

THP-1 Human Macrophage Cell Line (THP-1 cells)

Because THP-1 cells are deficient in CD14 on their surface, a stably transfected cell line of THP-1 with CD14 may be used (Werts et al., *Nat. Immunol.* 2:346-352, 2001; originally obtained from R. Ulevitch (Scripps Clinic)). Cells can be grown and maintained in RPMI in the presence of fetal calf serum (or autologous serum), and washed and the media may be replaced with media containing no serum, mouse serum, human serum, or fetal calf serum for the experiments. Results obtained from cells maintained in fetal calf serum may be compared with those maintained in autologous serum.

Mouse Alveolar Macrophages (MAVs)

MAVs may be prepared essentially as described by Salez et al. (*J. Leukoc. Biol.* 67:545-552, 2000). Cells can be prepared from bronchoalveolar lavage fluid (8 washes of 0.5 ml each) from 7-week old mice immediately after sacrifice. Differential cell numbers may be assessed by staining of aliquots, and purity can be determined by FACS analysis.

Human Peripheral Blood Mononuclear Cells (HPBMCs)

HPBMCs can be prepared by Ficoll-Hypaque density gradient centrifugation. PBMCs may be washed and suspended in RPMI medium. In some experiments, after Ficoll-Hypaque centrifugation, monocytes may be prepared by aggregation at 4° C. followed by rosetting with sheep red blood cells (Petit-Bertron et al., *J. Leukoc. Biol.* 73:145-154, 2003; Armant et al., *J. Immunol.* 155:4868-4875, 1995). In other experiments, monocytes may be prepared by magnetic depletion of other cells using an anti-lineage antibody cocktail (CD7, CD19, CD45RA, CD56, and anti-IgE antibodies) and passage through a magnetic column. The flow through containing the enriched monocyte population may be centrifuged, and monocytes may be washed in medium. Cells may be plated in 96-well plates at a density of 5-6×10$^5$ cells/cm$^2$. Purity of cells can be determined by FACS analysis. The media may be replaced with media containing fetal calf, mouse, or human serum prior to stimulation.

Cellular Activators

Multiple microbial products, including LPS, bacterial lipoproteins, CpG DNA, lipoteichoic acid, and peptidoglycan and whole bacteria have been reported to stimulate inflammation. These different stimulants may be selectively used according to the goal of the experiments.

LPS

LPS derived from *Escherichia coli* O111:B4 was purchased from Sigma Chemical, St Louis, Mo. or List Co (Campbell, Calif.). LPS may be further purified to remove contaminating proteins (Manthey and Vogel, *J. Endotoxin Res.* 1:84-91, 1994).

Pam3Cys

Pam3Cys that has been synthetically manufactured may be purchased from EMC Microcollection, Tubingen, Germany and used as a TLR-2 agonist.

Peptidoglycan-Associated Lipoprotein (PAL)

PAL is an outer membrane protein involved in maintaining cell wall integrity (Lazzaroni and Portalier, *Mol. Microbiol.* 6:735-742, 1992; Vianney et al., *J. Bacteriol.* 178:4031-4038, 1996; Mizuno T., *J. Biochem.* 86:991-1000, 1979). PAL induces pro-inflammatory cytokines in low nanogram concentrations (Hellman et al., *J. Biol. Chem.* 277:14274-14280, 2002) and activates endothelial cells (unpublished data). PAL may be purified from *E. coli* as described in Hellman et al. (*J. Biol. Chem.* 277:14274-14280, 2002).

Flagellin

Flagellin from *E. coli* and *S. muenchen* may be purchased from Inotek (Beverly, Mass.). Material free of LPS by passage over anti-LPS columns may also be purchased from this vendor.

CpG DNA

Phosphodiester oligonucleotides, including activating oligodeoxynucleotide and non-activating oligodeoxynucleotide can be purchased from Sigma-Genosys.

Peptidoglycan (PG)

PG may be purchased from Toxin Technology (Sarasota, Fla.) and can be analyzed for contaminating LPS by LAL, and for contaminating outer membrane proteins by immunoblotting with anti-PAL, anti-MLP, and anti-OmpA antibodies.

Heat-Killed Bacteria

Heat-killed *E. coli* O111:B4, *E. coli* O18, and *S. aureus* Cowan strain can be prepared by growing the strain in appropriate broth, washing the bacteria extensively by centrifugation, counting the bacteria by dilution and plating the bacteria on agar. The bacteria are killed by boiling, washed again, lyophilized, and weighed.

Cytokine Assays

Mouse TNF concentrations were measured using a Duoset ELISA kit for mouse TNF (R&D Systems; Minneapolis, Minn.). Human IL-6 concentrations can be measured using Duoset ELISA kit for human IL-6 (R&D Systems; Minneapolis, Minn.). ELISAs are performed following the manufacturer's protocol.

A mouse IL-6 sandwich ELISA can be carried out using rat IgG anti-IL-6 as a capture antibody (R&D Systems; Minneapolis, Minn.) and goat IgG anti-IL-6 as a detection antibody (R&D Systems; Minneapolis, Minn.). A similar protocol may be used as for the R&D Duoset ELISA kit.

Example 4

Treatment of a Chronic or Acute Inflammatory Response

The present invention features method of reducing or preventing, in a mammal (e.g., a human), a chronic inflammatory response such as inflammatory bowel disease, rheumatoid arthritis, or psoriasis or an acute inflammatory response that does not involve sepsis such as an inflammatory response resulting from an injury. In general, these methods involve administration of a compound (e.g., Apolipoprotein A2 or Apolipoprotein C3 (either purified or recombinantly expressed)) in an amount sufficient to reduce or prevent the chronic or acute inflammatory response. In desirable embodiments, Apolipoprotein A2 and Apolipoprotein C3 are administered together or in combination with another protein. Administration of the compound(s) may decrease a cytokine response in the mammal, including a decrease in TNFα, IL-6, or IL-8 expression or activity. Alternatively administration of the compound(s) may increase a cytokine response, including an increase in IL-10 expression or activity. Inflammatory responses that may be treated by administration of the compounds include, for example, those involving p38 MAP kinase, erk1/2, and NF-κB activation.

The compound is typically administered to the subject by means of injection using any routes of administration such as by intrathecal, subcutaneous, submucosal, or intracavitary injection as well as for intravenous or intraarterial injection. Thus, the compound may be injected systemically, for example, by the intravenous injection of the compound into the subject's bloodstream or alternatively, the compound can be directly injected at the site of an inflammation.

The compound(s) may be administered to the subject in a single dose or in multiple doses. When multiple doses are administered, the doses may be separated from one another by, for example, one day, two days, one week, two weeks, or one month. For example, a compound that modulates a cytokine response may be administered once a week for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compound. For example, the dosage of a compound that modulates a cytokine response can be increased if the lower dose does not provide sufficient anti-inflammatory activity. Conversely, the dosage of a compound that modulates a cytokine response can be decreased if the inflammation is cleared from the subject.

While the attending physician ultimately will decide the appropriate amount and dosage regimen, a therapeutically effective amount of a compound that modulates a cytokine response, may be, for example, in the range of about 0.0035 µg to 20 µg/kg body weight/day or 0.010 µg to 140 µg/kg body weight/week. Desirably a therapeutically effective amount is in the range of about 0.025 µg to 10 µg/kg, for example, about 0.025, 0.035, 0.05, 0.075, 0.1, 0.25, 0.5, 1.0, 1.5, 2.0, 2.5, 3.0, 3.5, 4.0, 5.0, 6.0, 7.0, 8.0, or 9.0 µg/kg body weight administered daily, every other day, or twice a week. In addition, a therapeutically effective amount may be in the range of about 0.05, 0.7, 0.15, 0.2, 1.0, 2.0, 3.0, 4.0, 5.0, 6.0, 7.0, 8.0, 10.0, 12.0, 14.0, 16.0, or 18.0 µg/kg body weight administered weekly, every other week, or once a month. Furthermore, a therapeutically effective amount of a compound that modulates a cytokine response may be, for example in the range of about 100 µg/m$^2$ to 100,000 µg/m$^2$ administered every other day, once weekly, or every other week. In a desirable embodiment, the therapeutically effective amount is in the range of about 1,000 µg/m² to 20,000 µg/m², for example, about 1,000, 1,500, 4,000, or 14,000 µg/m² of a compound that modulates a cytokine response administered daily, every other day, twice weekly, weekly, or every other week.

The administration of a compound that modulates a cytokine response may be by any suitable means that results in a concentration of the compound that modulates a cytokine response that, combined with other components, has anti-inflammatory properties upon reaching the target region. The compound may be contained in any appropriate amount in any suitable carrier substance, and is generally present in an amount of 1-95% by weight of the total weight of the composition. The composition may be provided in a dosage form that is suitable for parenteral (e.g., subcutaneous, intravenous, intramuscular, or intraperitoneal) administration route. The pharmaceutical compositions may be formulated according to conventional pharmaceutical practice (see, e.g., Remington: The Science and Practice of Pharmacy (20th ed.), ed. A. R. Gennaro, Lippincott Williams & Wilkins, 2000 and Encyclopedia of Pharmaceutical Technology, eds. J. Swarbrick and J. C. Boylan, 1988-1999, Marcel Dekker, New York).

Pharmaceutical compositions containing Apolipoprotein A2 and/or Apolipoprotein C3 as the active compound may be formulated to release the active compound immediately upon administration or at any predetermined time or time period after administration. The latter types of compositions are generally known as controlled release formulations. A pharmaceutical composition may be in a form suitable for sterile injection. To prepare such a composition, the suitable compound that modulates a cytokine response is dissolved or suspended in a parenterally acceptable liquid vehicle. Among acceptable vehicles and solvents that may be employed are water, water adjusted to a suitable pH by addition of an appropriate amount of hydrochloric acid, sodium hydroxide or a suitable buffer, 1,3-butanediol, Ringer's solution, dextrose solution, and isotonic sodium chloride solution. The aqueous formulation may also contain one or more preservatives (e.g., methyl, ethyl, or n-propyl p-hydroxybenzoate). In cases where one of the compounds is only sparingly or slightly soluble in water, a dissolution enhancing or solubilizing agent can be added, or the solvent may include 10-60% w/w of propylene glycol or the like.

All patents, patent applications, and publications mentioned in this specification are herein incorporated by reference to the same extent as if each independent patent, patent application, or publication was specifically and individually indicated to be incorporated by reference.

What is claimed is:

1. A method of reducing an acute inflammatory response in a mammal in need thereof, wherein said acute inflammatory response does not involve sepsis, said method comprising administering to said mammal a wild-type apolipoprotein A2 amino acid sequence in an amount sufficient to reduce said acute inflammatory response.

2. The method of claim 1 wherein said inflammatory response is from an injury.

3. The method of claim 2, wherein said injury is a burn.

4. The method of claim 1, wherein said inflammatory response is from, ischemic reperfusion injury or coronary bypass related illness.

5. The method of claim 1, wherein said mammal is a human.

6. The method of claim 1, wherein said apolipoprotein A2 amino acid sequence is a human apolipoprotein A2 amino acid sequence.

* * * * *